(12) United States Patent
Baloch et al.

(10) Patent No.: US 9,367,667 B2
(45) Date of Patent: Jun. 14, 2016

(54) METHOD AND SYSTEM FOR ADVANCED ANEURYSM ANALYSIS

(71) Applicant: Siemens Aktiengesellschaft, Munich (DE)

(72) Inventors: Sajjad Hussain Baloch, Novi, MI (US); Erkang Cheng, Elkins Park, PA (US); Ying Julie Zhu, Monmouth Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 171 days.

(21) Appl. No.: 14/266,306

(22) Filed: Apr. 30, 2014

(65) Prior Publication Data

US 2015/0317442 A1    Nov. 5, 2015

(51) Int. Cl.
G06N 7/08    (2006.01)
G06F 19/00    (2011.01)
G06N 7/00    (2006.01)
G06N 99/00    (2010.01)

(52) U.S. Cl.
CPC .............. *G06F 19/345* (2013.01); *G06N 7/005* (2013.01); *G06N 99/005* (2013.01); *G06N 7/08* (2013.01)

(58) Field of Classification Search
None
See application file for complete search history.

(56) References Cited

PUBLICATIONS

Kohout, et al., Aneurysm Identification by Analysis of the Blood-Vessel Skeleton, Computer Methods and Programs in Biomedicine 109 (2013) pp. 32-47.*
Baloch et al. "A System for Saccular Intracranial Aneurysm Analysis and Virtual Stent Planning" SPIE Medical Imaging 2012; 2012.
Baloch et al. "Shape Based Conditional Random Fields for Segmenting Intracranial Aneurysms" MICCAI 2011; 2011.

* cited by examiner

*Primary Examiner* — Wilbert L Starks

(57) ABSTRACT

An automated method for aneurysm analysis including: extracting shape descriptors from test vessel data; generating an aneurysm probability map for the test vessel data using the shape descriptors; detecting the presence of the aneurysm on the test vessel data; localizing the aneurysm in the probability map; and separating the aneurysm from the probability map.

20 Claims, 7 Drawing Sheets

METHOD AND SYSTEM FOR ADVANCED ANEURYSM ANALYSIS

TECHNICAL FIELD

The present invention relates to advanced aneurysm analysis, and more particularly, to a framework for aneurysm detection, localization, separation and treatment planning.

DISCUSSION OF THE RELATED ART

An aneurysm is a localized, blood-filled balloon-like bulge in the wall of a blood vessel such as an artery. An aneurysm can grow large and rupture (burst) or dissect. A rupture causes dangerous bleeding inside the body. A dissection is a split in one or more layers of the artery wall. The split causes bleeding into and along the layers of the artery wall. Both rupture and dissection often are fatal.

In order to prevent an aneurysm's growth and reduce the risk of its rupture, surgical intervention is required, where stents, wire coils, and other embolic material or devices are placed not only to enforce the vessel wall, but also to alter the blood flow pattern, thereby reducing the pressure on regions more prone to rupture.

An aneurysm is detected manually by visually inspecting an X-ray, or more advanced three-dimensional (3D) imaging modalities such as computed tomography (CT). The user then manually determines the volume of interest to focus the aneurysm. The dome point of the aneurysm is also selected manually. The aneurysm may be automatically separated, but such separation methods are not robust and are sensitive to seed points (dome point/proximal and distal points). As pertains to treatment planning, the actual physical stent is not used, but rather, a visual sketch is used that does not conform to the vessel walls.

SUMMARY OF THE INVENTION

According to an exemplary embodiment of the present invention, an automated method for aneurysm analysis comprises: extracting shape descriptors from test vessel data; generating an aneurysm probability map for the test vessel data using the shape descriptors; detecting the presence of the aneurysm on the test vessel data; localizing the aneurysm in the probability map; and separating the aneurysm from the probability map.

The shape descriptors are extracted to capture local geometric and regional shape information of the aneurysm.

The probability map is generated by using learned properties of the extracted information.

The presence of the aneurysm is detected by finding if the probability map has a value greater than a minimum probability threshold.

The aneurysm is localized by determining the most probable aneurysm location from the probability map if the aneurysm is detected.

The aneurysm is separated from the probability map by executing a separation algorithm on a region of interest including the aneurysm.

The separation algorithm automatically finds the region of interest, and proximal and distal points.

The method further comprises quantifying the aneurysm.

The method further comprises planning a surgical procedure by using the aneurysm.

The method further comprises: localizing another aneurysm in the probability map; and separating the another aneurysm from the probability map.

According to an exemplary embodiment of the present invention, a system for automated aneurysm analysis comprises: a memory device for storing a program; a processor in communication with the memory device, the processor operative with the program to: extract shape descriptors from test vessel data; generate an aneurysm probability map for the test vessel data using the shape descriptors; detect the presence of the aneurysm on the test vessel data; localize the aneurysm in the probability map; and separate the aneurysm from the probability map.

The shape descriptors are extracted to capture local geometric and regional shape information of the aneurysm.

The probability map is generated by using learned properties of the extracted information.

The presence of the aneurysm is detected by finding if the probability map has a value greater than a minimum probability threshold.

The aneurysm is localized by determining the most probable aneurysm location from the probability map if the aneurysm is detected.

The aneurysm is separated from the probability map by executing a separation algorithm on a region of interest including the aneurysm.

The separation algorithm automatically finds the region of interest, and proximal and distal points.

The processor is further operative with the program to quantify the aneurysm.

The processor is further operative with the program to plan a surgical procedure by using the aneurysm.

The processor is further operative with the program to: localize another aneurysm in the probability map; and separate the another aneurysm from the probability map.

DETAILED DESCRIPTION OF EXEMPLARY EMBODIMENTS

The present invention discloses a framework for (1) the detection of aneurysm(s) in a vessel tree; (2) the localization of aneurysms for auto-volume of interest (VOI) selection, and auto-detection of the dome point; (3) the robust separation of aneurysms; and (4) treatment planning via actual stent deployment.

Figure 1:
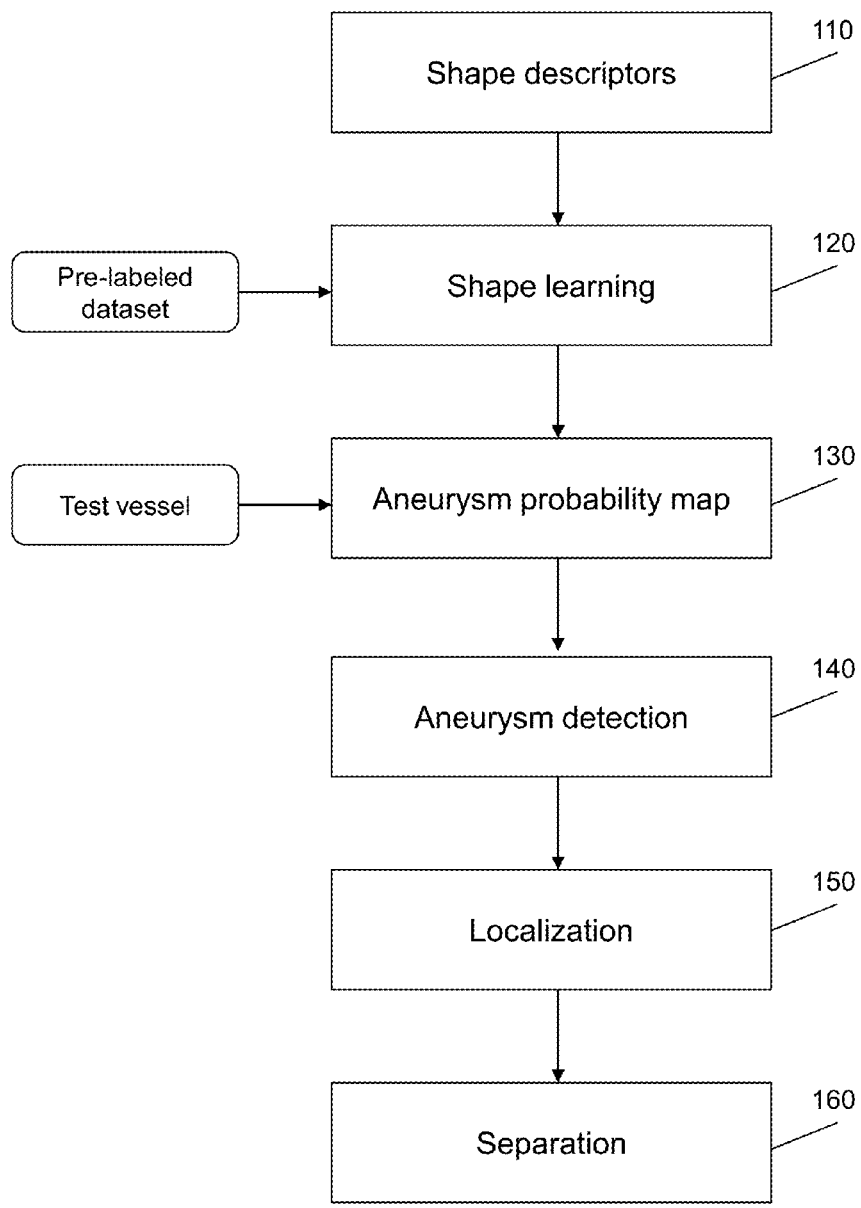
FIG. 1 is a flowchart showing an automated approach to aneurysm localization and separation according to an exemplary embodiment of the present invention.

FIG. 1 is a flowchart showing an automated approach to aneurysm localization and separation according to an exemplary embodiment of the present invention.

In step (110) illustrated in FIG. 1, shape descriptors that can be used to identify an aneurysm are extracted from a database. The database may store, inter alia, geometric properties of an aneurysm's shape. For example, in the database there may be included geometric properties of aneurysms with the following shapes: multi-lobed, fusiform, angled and kissing vessel, and the geometric properties of healthy vessels. In the following discussion, it is assumed that shape descriptors for one aneurysm shape were extracted.

The shape descriptors may be extracted considering the local geometric information such as various curvatures and shape index, as well as regional shape such as Wilmore Energy, and attribute weighted geodesic shape contexts, using the approach described in Baloch et al., "Shape based Conditional Random Fields for Segmenting Intracranial Aneurysms," MICCAI 2011, the disclosure of which is incorporated by reference herein in its entirety.

In step (120) illustrated in FIG. 1, shape learning takes place. In this step, a pre-labeled dataset of similar aneurysms and vessels is used in conjunction with the extracted shape descriptors to model aneurysm and vessel shape characteristics. In particular, a classifier, such as randomized decision forest, is determined which can label each point on a vessel as healthy or not.

In step (130) illustrated in FIG. 1, test vessel data in the form of vessel surface representation is input (e.g., a 3D CT image of a person, where the vessel tree is extracted using volumetric segmentation, and 3D digital subtraction imaging may be used to enhance vessel contrast for accurate segmentation) and using the test vessel data and learned properties, an aneurysm probability map is created. For example, the classifier is used to create the probability map such that for each point on the vessel surfaces shown there will be a probability indicative of whether or not an aneurysm is present. The probability map may be computed using the approach described in Baloch et al., "Shape based Conditional Random Fields for Segmenting Intracranial Aneurysms," MICCAI 2011.

Figure 3:
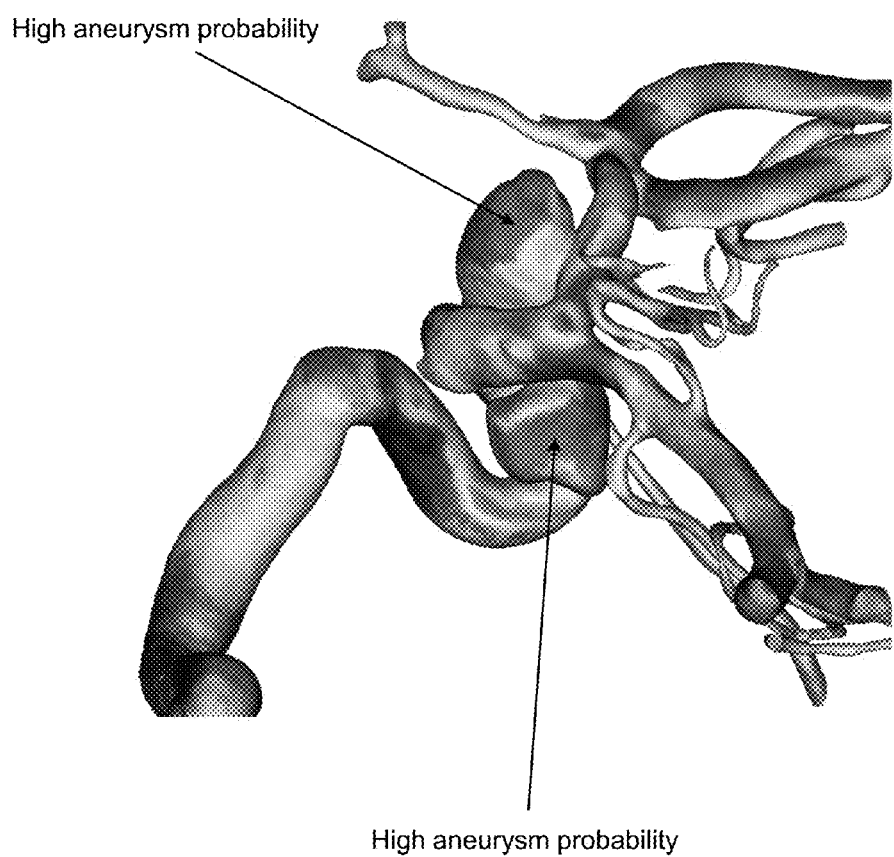
FIG. 3 is a probability map computed in accordance with an exemplary embodiment of the present invention.

An example of a probability map is shown in FIG. 3. The probability map can be colored to highlight areas of high aneurysm probability and low aneurysm probability. Since the map is in black and white to conform to USPTO guidelines, only areas of high aneurysm probability are indicated in FIG. 3.

In step (140) illustrated in FIG. 1, the presence of aneurysm is detected from the probability map. If the probability map has a value less than a pre-specified threshold, which is learned in step (120) using techniques such as maximizing the area under a receiver operating characteristic (ROC) curve, it is decided that the aneurysm is not present. An aneurysm is detected/diagnosed, if probabilities greater than the threshold are encountered.

Figure 4:
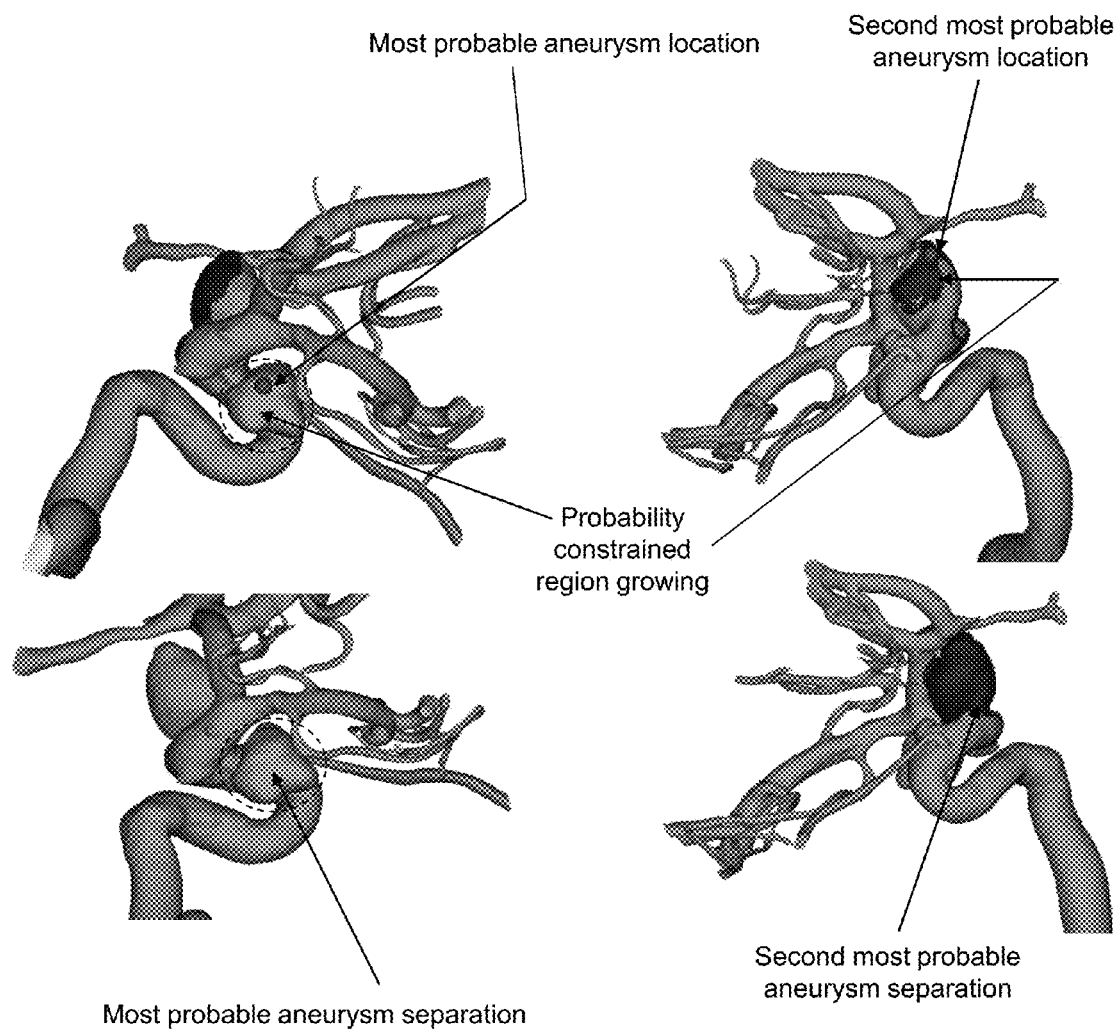
FIG. 4 is a diagram illustrating aneurysm localization and separation according to an exemplary embodiment of the present invention.

In step (150) illustrated in FIG. 1, the aneurysm is localized. In this step, the most probable aneurysm location is determined from the probability map. FIG. 4 illustrates an example of the most probable aneurysm location in a probability map (see upper left hand corner vessels). When the most probable aneurysm location is identified, a region of interest (ROI) surrounding the most probable aneurysm location may be subject to a probability constrained region growing. The region grown area is illustrated in FIG. 4 within a dashed circle (see upper left hand corner vessels).

In step (160) illustrated in FIG. 1, the aneurysm is separated from the healthy vessel with the ROI. In this step, a separation algorithm (discussed hereafter with reference to FIG. 5) is used to separate the aneurysm from the healthy vessel. The resulting aneurysm is illustrated in FIG. 4 (see lower left hand corner vessels).

Figure 2:
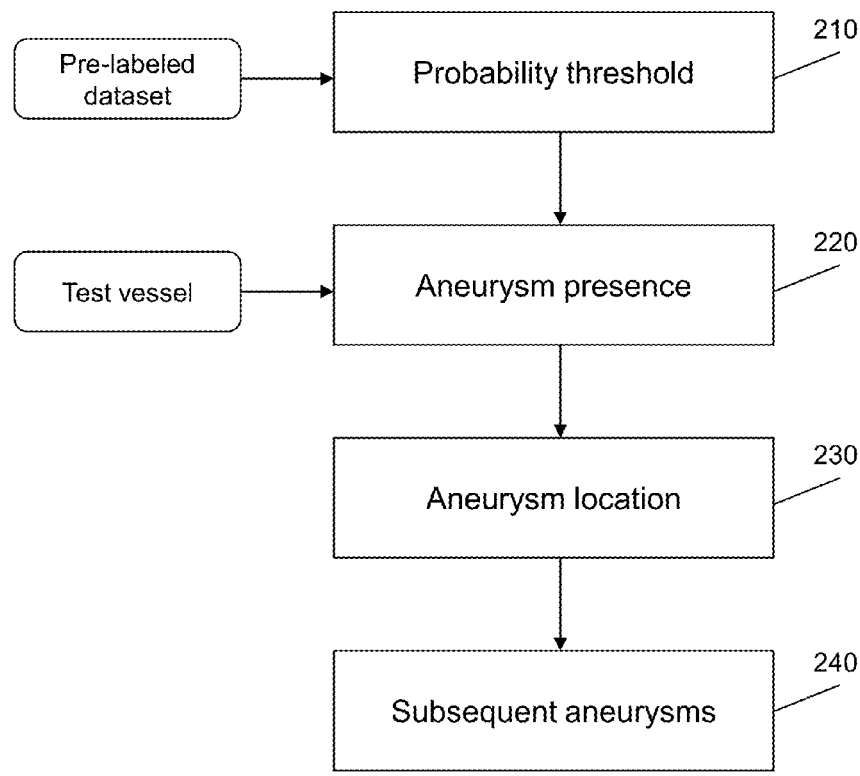
FIG. 2 is a flowchart showing aneurysm detection according to an exemplary embodiment of the present invention.

FIG. 2 is a flowchart showing aneurysm detection according to an exemplary embodiment of the present invention. In particular, FIG. 2 illustrates parts of steps 120-140 of FIG. 1 in more detail.

In step (210) illustrated in FIG. 2, using the pre-labeled dataset, a probability threshold is determined. In this step, minimum aneurysm probability is determined using the learned dataset. A user may manually change the threshold value.

In step (220) illustrated in FIG. 2, applying the probability threshold to the test vessel data, aneurysm presence is detected. In this step, an aneurysm may exist if a probability greater than the threshold exists.

In step (230) illustrated in FIG. 2, the location of the aneurysm is determined. In this step, the most probable aneurysm location is determined from the probability map using the aneurysm results. Here, the aforementioned probability based region growing is performed. Focus is only on the probabilities greater than the threshold.

In step (240) illustrated in FIG. 2, subsequent aneurysms may be determined. In this step, it is determined if a second most probable aneurysm location exists, excluding the first aneurysm region, such that there is a probability value greater than the threshold elsewhere on the test vessel data. The same process used to determine the most probable aneurysm location may be used to determine the second most probable aneurysm location. Similarly, the same process used to separate the most probable aneurysm location may be the same as that used to separate the second most probably aneurysm location. FIG. 4 illustrates an example of the location of the second most probable aneurysm location (upper right hand corner vessels) and the probability map with the second aneurysm gone (lower right hand corner vessels). The process is repeated until no point on the vessel is found with a probability map value greater than the threshold, after excluding the previously identified regions.

Figure 5:
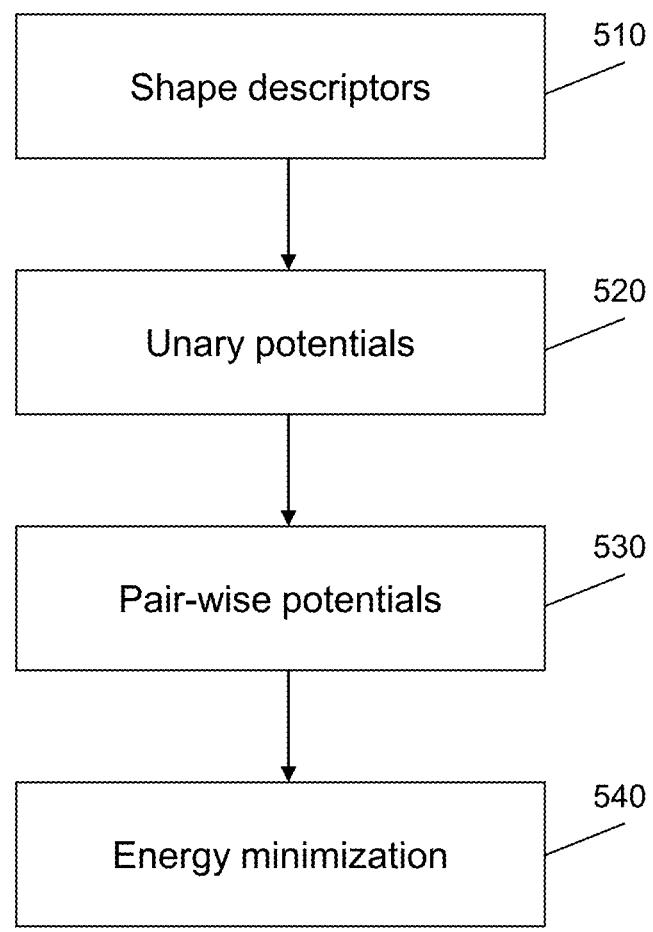
FIG. 5 is flowchart illustrating an aneurysm separation algorithm according to an exemplary embodiment of the present invention.
Figure 6:
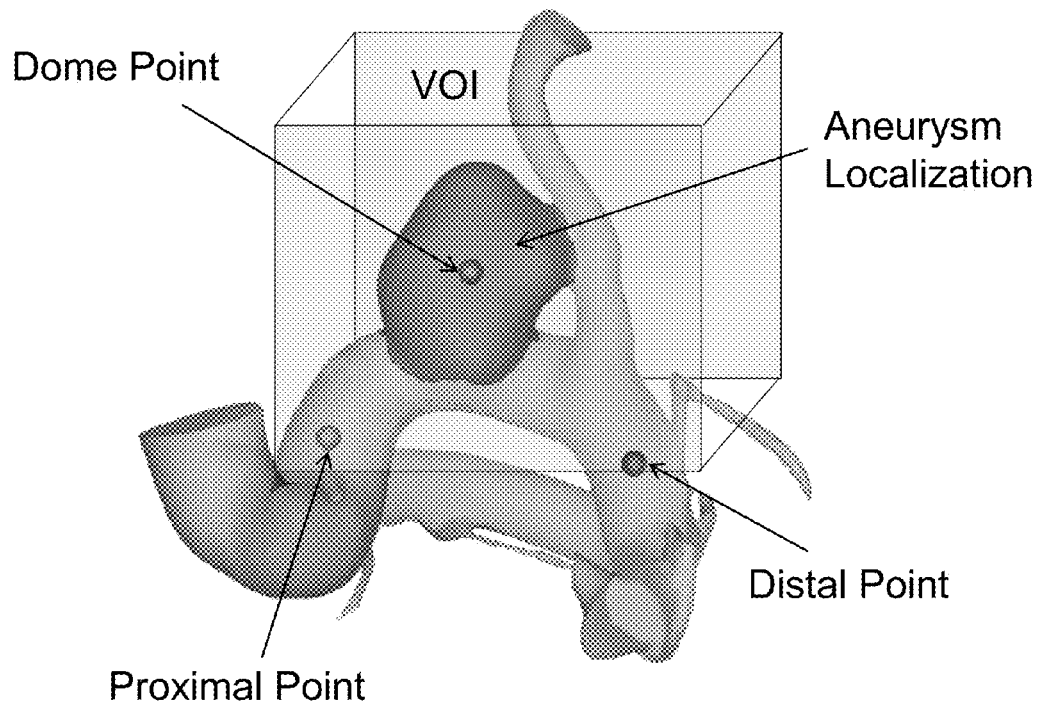
FIG. 6 is a diagram for explaining the aneurysm separation algorithm of FIG. 5 according to an exemplary embodiment of the present invention.

FIG. 5 is flowchart illustrating the details of an aneurysm separation algorithm of step (160) of FIG. 1, according to an exemplary embodiment of the present invention. The aneurysm separation algorithm operates on the results from the preceding steps of FIG. 1. The center of the aneurysm localization is henceforth considered as the dome point, a bounding box around the probability constrained region growing of the aneurysm localization step is the volume of interest (VOI), and the extents of the healthy vessel within this VOI are tagged as the proximal and distal points as illustrated in FIG. 6.

In step (510) illustrated in FIG. 5, shape descriptors that can be used to identify an aneurysm are extracted from a database. The database may store, inter alia, geometric properties of an aneurysm's shape viz-a-viz the healthy vessel. The shape descriptors may be extracted considering the local geometric information such as various curvatures and shape index, as well as regional shape information such as Wilmore Energy, and attribute weighted geodesic shape contexts. Geodesic shape contexts are constructed based on uniform binning of the geodesic distance based distribution, and attribute weighting is done by augmenting the bins via surface area within a bin, and/or counting the number of connected components within each bin. A final feature in the shape descriptor may be composed of the visibility of a point from the reference point, where the dome point is used as the reference point.

In step (520) illustrated in FIG. 5, unary potentials are computed. Two types of unary potentials are considered. A weak unary potential is based on the probability map computed in step (130) of FIG. 1, and illustrated in FIG. 3. A strong unary potential is based on the intersection of the test vessel data with three planes defined at the dome and the proximal and distal points. The first plane provides the aneurysm strong prior and is defined using the approach described in Baloch et al., "Shape based Conditional Random Fields for Segmenting Intracranial Aneurysms," MICCAI 2011. The remaining two planes provide a healthy vessel strong prior, and their plane normals are computed by a cross-sectional area minimizing algorithm.

In step (530) illustrated in FIG. 5, pairwise potentials are computed based on the local curvature (high curvature means high potential), smoothness constraints, as well as layout constraints, where layout is imposed in terms of the geodesic distance.

In step (540) illustrated in FIG. 5, unary and pairwise potentials are combined to formulate an energy functional that depends on the label assignment. Optimization of this energy functional is carried out using a graph cut algorithm to find the optimal labeling (aneurysm labels and healthy vessel labels on the surface).

Once the aneurysm is separated from the healthy vessel, the aneurysm is quantified via various measurements for evaluation by a physician. Subsequently, in the surgical planning step, a stent deployment planning may be carried out automatically by first reconstructing the healthy vessel (by removing the aneurysm using an approach similar to that described in Baloch et al., "A System for Saccular Intracranial Aneurysm Analysis and Virtual Stent Planning," SPIE Medical Imaging 2012, the disclosure of which is incorporated by reference herein in its entirety), extracting its centerline between the proximal and dome point, and using it to define an axial deformation profile for a stent model. Finally, the radial deformation may be carried out by expanding the stent model within the vessel with a force that is proportional to the pointwise difference between the stent mesh and its corresponding points on the healthy vessel model. Stiffness of the stent model surface is maintained via smoothness constraints.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article or manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 7:
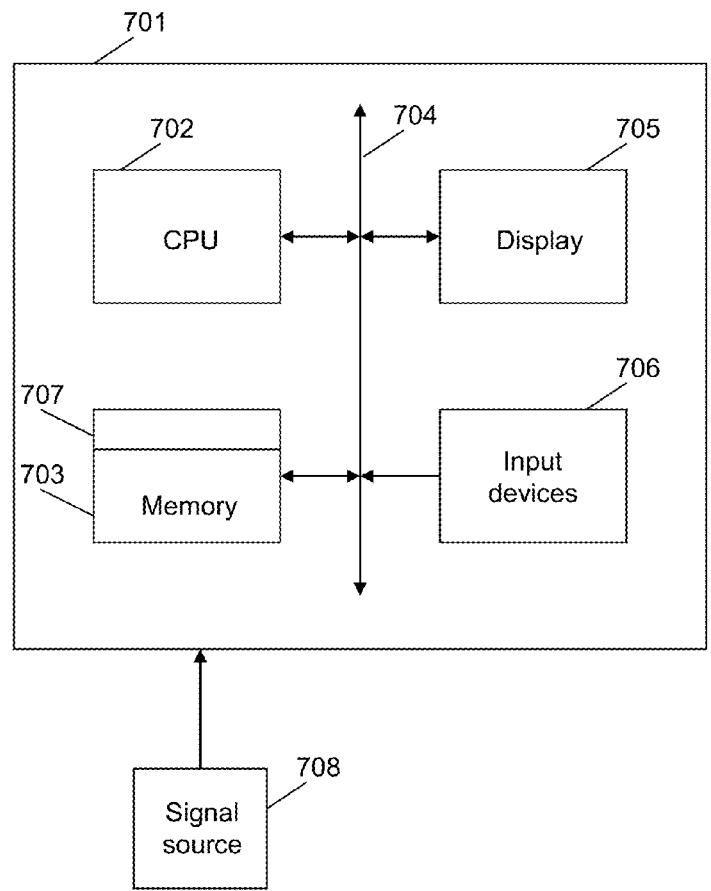
FIG. 7 is a computer system in which an exemplary embodiment of the present invention may be implemented.

Referring now to FIG. 7, according to an exemplary embodiment of the present invention, a computer system 701 can comprise, inter alia, a central processing unit (CPU) 702, a memory 703 and an input/output (I/O) interface 704. The computer system 701 is generally coupled through the I/O interface 704 to a display 705 and various input devices 706 such as a mouse and keyboard. The support circuits can include circuits such as cache, power supplies, clock circuits, and a communications bus. The memory 703 can include RAM, ROM, disk drive, tape drive, etc., or a combination thereof. Exemplary embodiments of present invention may be implemented as a routine 707 stored in memory 703 (e.g., a non-transitory computer-readable storage medium) and executed by the CPU 702 to process the signal from a signal source 708. As such, the computer system 701 is a general-purpose computer system that becomes a specific purpose computer system when executing the routine 707 of the present invention.

The computer system 701 also includes an operating system and micro-instruction code. The various processes and functions described herein may either be part of the micro-instruction code or part of the application program (or a combination thereof) which is executed via the operating system. In addition, various other peripheral devices may be connected to the computer system 701 such as an additional data storage device and a printing device.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described to best explain the principles of the invention and the practical application, and to enable others of ordinary skill in the art to understand the invention for various embodiments with various modifications as are suited to the particular use contemplated.

What is claimed is:

1. An automated method for aneurysm analysis, comprising:
   extracting shape descriptors from test vessel data;
   generating an aneurysm probability map for the test vessel data using the shape descriptors;
   detecting the presence of the aneurysm on the test vessel data;
   localizing the aneurysm in the probability map; and
   separating the aneurysm from the probability map,
   wherein separating the aneurysm from the probability map comprises:
   extracting shape descriptors that can identify the aneurysm from a database;
   computing a weak unary potential based on the probability map and a strong unary potential based on the intersection of the test vessel data with three planes defined by a dome and proximal and distal points of the aneurysm;
   computing pairwise potentials;
   combining the weak and strong unary potentials with the pairwise potentials to formulate an energy function that depends on label assignment in the probability map; and
   optimizing the energy function.

2. The method of claim 1, wherein the shape descriptors are extracted to capture local geometric and regional shape information of the aneurysm.

3. The method of claim 2, wherein the probability map is generated by using learned properties of the extracted information.

4. The method of claim 1, wherein the presence of the aneurysm is detected by finding if the probability map has a value greater than a minimum probability threshold.

5. The method of claim 1, wherein the aneurysm is localized by determining the most probable aneurysm location from the probability map if the aneurysm is detected.

6. The method of claim 1, wherein the aneurysm is separated from the probability map by executing a separation algorithm on a region of interest including the aneurysm.

7. The method of claim 6, wherein the separation algorithm automatically finds the region of interest, and the proximal and distal points.

8. The method of claim 1, further comprising quantifying the aneurysm.

9. The method of claim 1, further comprising planning a surgical procedure by using the aneurysm.

10. The method of claim 1, further comprising:
    localizing another aneurysm in the probability map; and
    separating the another aneurysm from the probability map.

11. A system for automated aneurysm analysis, comprising:
    a memory device for storing a program;
    a processor in communication with the memory device, the processor operative with the program to:
    extract shape descriptors from test vessel data;
    generate an aneurysm probability map for the test vessel data using the shape descriptors;
    detect the presence of the aneurysm on the test vessel data;
    localize the aneurysm in the probability map; and
    separate the aneurysm from the probability map, wherein the processor is further operative with the program when separating the aneurysm from the probability map to:

extract shape descriptors that can identify the aneurysm from a database;

compute a weak unary potential based on the probability map and a strong unary potential based on the intersection of the test vessel data with three planes defined by a dome and proximal and distal points of the aneurysm;

compute pairwise potentials;

combine the weak and strong unary potentials with the pairwise potentials to formulate an energy function that depends on label assignment in the probability map; and optimize the energy function.

12. The system of claim 11, wherein the shape descriptors are extracted to capture local geometric and regional shape information of the aneurysm.

13. The system of claim 12, wherein the probability map is generated by using learned properties of the extracted information.

14. The system of claim 11, wherein the presence of the aneurysm is detected by finding if the probability map has a value greater than a minimum probability threshold.

15. The system of claim 11, wherein the aneurysm is localized by determining the most probable aneurysm location from the probability map if the aneurysm is detected.

16. The system of claim 11, wherein the aneurysm is separated from the probability map by executing a separation algorithm on a region of interest including the aneurysm.

17. The system of claim 16, wherein the separation algorithm automatically finds the region of interest, and the proximal and distal points.

18. The system of claim 11, wherein the processor is further operative with the program to quantify the aneurysm.

19. The system of claim 11, wherein the processor is further operative with the program to plan a surgical procedure by using the aneurysm.

20. The system of claim 11, wherein the processor is further operative with the program to:

localize another aneurysm in the probability map; and separate the another aneurysm from the probability map.

* * * * *